United States Patent [19]

Kleinknecht

[11] 4,211,488
[45] Jul. 8, 1980

[54] OPTICAL TESTING OF A SEMICONDUCTOR

[75] Inventor: Hans P. Kleinknecht, Bergdietikon, Switzerland

[73] Assignee: RCA Corporation, New York, N.Y.

[21] Appl. No.: 948,107

[22] Filed: Oct. 3, 1978

[51] Int. Cl.$^2$ .......................................... G01N 21/32
[52] U.S. Cl. .................................. 356/369; 250/571; 356/237; 356/402
[58] Field of Search ................ 356/51, 317, 318, 402, 356/414, 420, 407, 237; 250/341, 571

[56] References Cited

U.S. PATENT DOCUMENTS

| 3,555,455 | 1/1971 | Gruber et al. | 331/94.5 |
| 3,988,564 | 10/1976 | Garvin et al. | 219/121 EM |

OTHER PUBLICATIONS

Sooy, W. R. et al., "Switching of Semiconductor Reflectivity by a Giant Pulse Laser", *Applied Physics Letters*, vol. 5, No. 3, pp. 54–56, Aug. 1, 1964.
Sosnowski, L., "Contribution of Current Carriers in the Reflection of Light from Semiconductors", *Physical Review* vol. 107, No. 4, Aug. 15, 1957.
Birnbaum, "Modulation of the Reflectivity of Semiconductors," *Journal of Applied Physics*, pp. 652–658, vol. 36, No. 2.
Rassudova et al., "Precision Diffraction Gratings for Metrologic Purposes", Optics and Spectroscopy, Aug. 1961, pp. 136–137.
Vasil'eva et al., Measurement of the Selective Growth and Etching Rates of GaAs, Inorganic Materials, vol. 12, Feb. 1976, pp. 162–164.

Primary Examiner—John K. Corbin
Assistant Examiner—Bruce Y. Arnold
Attorney, Agent, or Firm—H. Christoffersen; D. S. Cohen; T. H. Magee

[57] ABSTRACT

A method of optically testing electrical parameters of a surface of a semiconductor including carrier mobility and recombination time is disclosed which includes the step of irradiating the surface with a first beam of monochromatic light having a wavelength less than the wavelength corresponding to the band-gap energy of the semiconductor, resulting in the excitation of electrons and holes at the semiconductor surface. The surface is simultaneously irradiated with a second beam of monochromatic light having a wavelength larger than the wavelength corresponding to the band-gap energy of the semiconductor, whereby part of the second beam is reflected from the surface. The intensity of this reflected beam is measured and the magnitude thereof is a measure of the carrier mobility and recombination time at the semiconductor surface.

10 Claims, 3 Drawing Figures

OPTICAL TESTING OF A SEMICONDUCTOR

This invention relates to a method of optically testing electrical parameters of a semiconductor surface including carrier mobility and recombination time.

The fabrication of integrated circuit (IC) devices involves many sophisticated processing steps such as polishing, etching, oxidation, masking, diffusion, metallization and bonding. However, in general, it is very difficult, expensive and time consuming to spot check, test and monitor all of these processes on the production line. Electrical testing cannot be done before the metallization has been made. Normally this is too late for correcting any preceding process which may have gone wrong, and it may be impossible then under factory conditions to find out which process step was at fault.

The yield in IC manufacturing could be improved significantly if one had a method for testing silicon wafers in room-temperature air between the various processing steps without the need for touching the wafers. What one needs to measure is not necessarily the electrical functioning of the circuit, but only one or two electrical parameters which are sensitive to variations of the process and particularly to the quality of the silicon surface and/or the silicon-silicon dioxide interface. The present invention provides an optical technique used to give a measure for the carrier mobility and the recombination time near the silicon surface.

The present novel invention utilizes the influence of free electrons and holes on the refractive index of a semiconductor material. The refractive index for a material is the ratio of the sine of the angle of incidence to the sine of the angle of refraction when a light ray passing through a vacuum (or for practical purposes air) strikes the surface of the material and is divided into a reflected ray and a refracted ray. The effectiveness of the semiconductor surface in reflecting light, i.e., its reflectivity, is thus influenced by the index of refraction for the semiconductor material and may be monitored by measuring the intensity of the reflected ray. The main idea of the present method is to excite high concentrations of free carriers in the surface layer of the semiconductor with a high-power laser of wavelength shorter than band gap. This induced free-carrier concentration will give a small decrease in the refractive index, which can be probed by simultaneously reflecting from the semiconductor surface a beam of a long-wavelength laser. The magnitude of this change and its time dependence will be determined by the carrier recombination time, $\tau$, and by the carrier mobility, $\mu$. Both of these parameters are sensitive to crystal perfection, doping and surface (or interface) condition, and will therefore be a good indicator of the process perfection.

Figure 1:
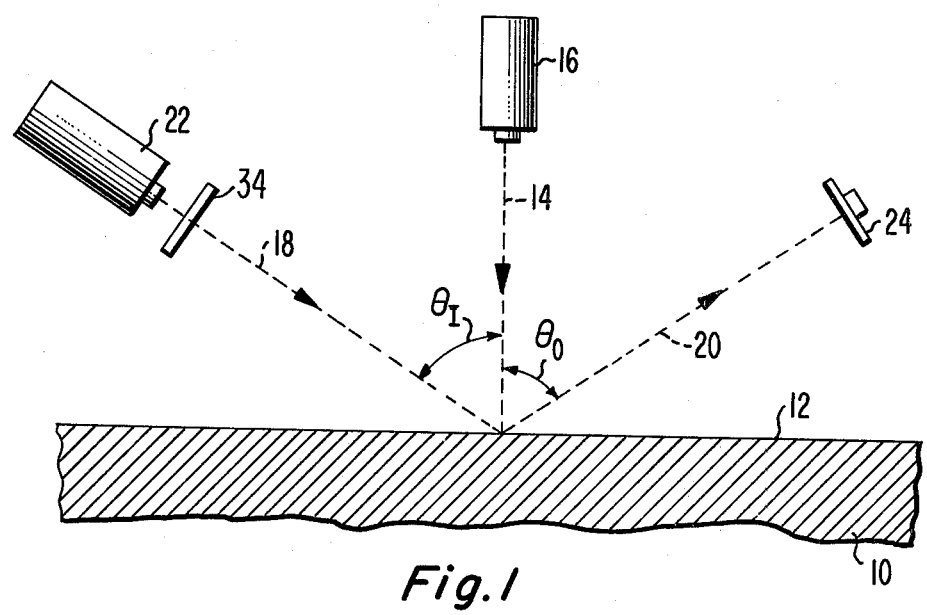
FIG. 1 is a cross-sectional view illustrating diagrammatically the use of two different laser beams in the present novel method.

Referring to FIG. 1 of the drawings, there is shown a substrate 10 of semiconductor material which may be part of a silicon wafer. In order to optically test various electrical parameters including carrier mobility, $\mu$ (average of the electrons and holes), and recombination time, $\tau$, near a surface 12 of the substrate 10, I disclose a method comprising irradiating an area of the surface 12 uniformly with a first beam 14 of monochromatic light, preferably a laser beam, having a wavelength $\lambda_1$ less than the wavelength corresponding to the band-gap energy of the semiconductor substrate 10. For silicon having a band-gap energy of 1.106 eV (electronvolt), the corresponding wavelength is 1.12 micrometers. If $\lambda_1$ is less than about 1 micrometer, substantially all of the light beam 14 energy is absorbed in a very thin layer adjacent the surface 12, resulting in the excitation of electrons and holes near the surface 12. This excitation could be done in principle with an ultraviolet nitrogen laser. However, the convenience of visible light for focusing purposes makes the use of a pulsed dye laser 16 ($\lambda_1=0.5$ micrometers), pumped by nitrogen, preferable for the first light beam 14. Under these conditions, the steady-state concentration, p, of free carriers is:

$$p = \frac{N_L\tau}{Ah\nu_1 L} = \frac{N_L\tau\lambda_1}{A(Hc)L} = \frac{N_L\tau\lambda_1}{(1.2)(A)(L)} = 3.4 \times 10^{17} N_L \text{ cm}^{-3}$$

where $N_L$ is the laser power, A is the spot area of the irradiated surface 12 which must have a diameter larger than L, and L is the carrier diffusion length equal to $\sqrt{D\tau}$ where D is the carrier diffusion constant. The number on the right-hand side is calculated for A=0.25 mm$^2$, $\lambda_1=0.5\mu$, $\tau=10^{-6}$ seconds and L=30$\mu$, if $N_L$ is written in watts. Values for p at different power levels, $N_L$, are listed at column two in Table I.

TABLE I

| LASER POWER $N_L$ | INDUCED FREE CARRIER CONCENTRATION p[cm$^{-3}$] | $\Delta$ | UNIFORM EXCITATION NORMAL REFLECTION $\Delta_1$ | REFLECTIVITY AT BREWSTER'S ANGLE $R_B$ | UNIFORM EXCITATION BREWSTER'S REFLECTION $\Delta_2$ | GRATING EXCITATION NORMAL REFLECTION $\Delta_3$ | GRATING EXCITATION BREWSTER'S REFLECTION $\Delta_4$ |
|---|---|---|---|---|---|---|---|
| 100 mW | $3.4 \times 10^{16}$ | $1.0 \times 10^{-4}$ | $1.3 \times 10^{-4}$ | $2.1 \times 10^{-9}$ | $1.3 \times 10^{-4}$ | $7.1 \times 10^{-8}$ | $2.2 \times 10^{-3}$ |
| 1 W | $3.4 \times 10^{17}$ | $1.0 \times 10^{-3}$ | $1.3 \times 10^{-3}$ | $2.1 \times 10^{-7}$ | $1.3 \times 10^{-2}$ | $7.1 \times 10^{-6}$ | $2.2 \times 10^{-1}$ |
| 10 W | $3.4 \times 10^{18}$ | $1.0 \times 10^{-2}$ | $1.3 \times 10^{-2}$ | $2.1 \times 10^{-5}$ | $1.3$ | $7.1 \times 10^{-4}$ | $2.2 \times 10^{1}$ |
| 100 W | $3.4 \times 10^{19}$ | $1.0 \times 10^{-1}$ | $1.3 \times 10^{-1}$ | $2.1 \times 10^{-3}$ | $1.3 \times 10^{2}$ | $7.1 \times 10^{-2}$ | $2.2 \times 10^{3}$ |
| 1 RW | $3.4 \times 10^{20}$ | $1.0$ | $1.3$ | $2.1 \times 10^{-1}$ | $1.3 \times 10^{4}$ | $7.1$ | $2.2 \times 10^{5}$ |

In order to avoid heating of the substrate 10, the first laser beam 14 should be pulsed such that the average power stays below about $\overline{N} \simeq 10$ milliwatts. With a practical pulse repetition frequency, $1/t_r$, of 10 cycles per second, this gives a pulse duration time of $t_p = t_r \overline{N}/N_L \simeq 100$ $\mu$sec.

The surface 12 of the substrate 10 is simultaneously irradiated with a second beam 18 of monochromatic light, preferably a second laser beam, having a wavelength $\lambda_2$ larger than the wavelength corresponding to the band-gap energy of silicon, whereby part of the second beam 18, shown as reflected beam 20, is reflected from the surface 12. As further explained below, the speed requirement for detecting the reflected beam 20 sets a limit for $\lambda_2$, since a fast semiconductor detector is utilized. Consequently, I use for the second laser beam 18 an infrared He-Ne laser 22 having a wavelength $\lambda_2$ equal to 3.39 micrometers.

The intensity of the reflected beam 20 is now measured by utilizing a photodetector. In the present embodiment, an InSb junction detector 24 is placed at an angular position to receive the reflected beam 20, as illustrated in FIG. 1. The InSb junction detector is a relatively fast semiconductor detector, which has a cut-off wavelength of 5.4 micrometers in liquid nitrogen and a cut-off of 5.0 micrometers in liquid helium. With a pulse duration time of about 100 $\mu$sec, the response time of the detector 24 has to be at least 100 $\mu$sec. The intensity of the reflected beam 20 is a measure of the carrier mobility and recombination time at the semiconductor surface 12 since the index of refraction, and through that, the reflectivity are affected by the induced free-carrier concentration. The magnitude of this change will be determined by the carrier recombination time, $\tau$, and by the carrier mobility, $\mu$, at the semiconductor surface. Both of these parameters are sensitive to conditions existing at semiconductor surface 12 including crystal perfection and doping level, and will therefore be good indicators of the process perfection.

Figure 3:
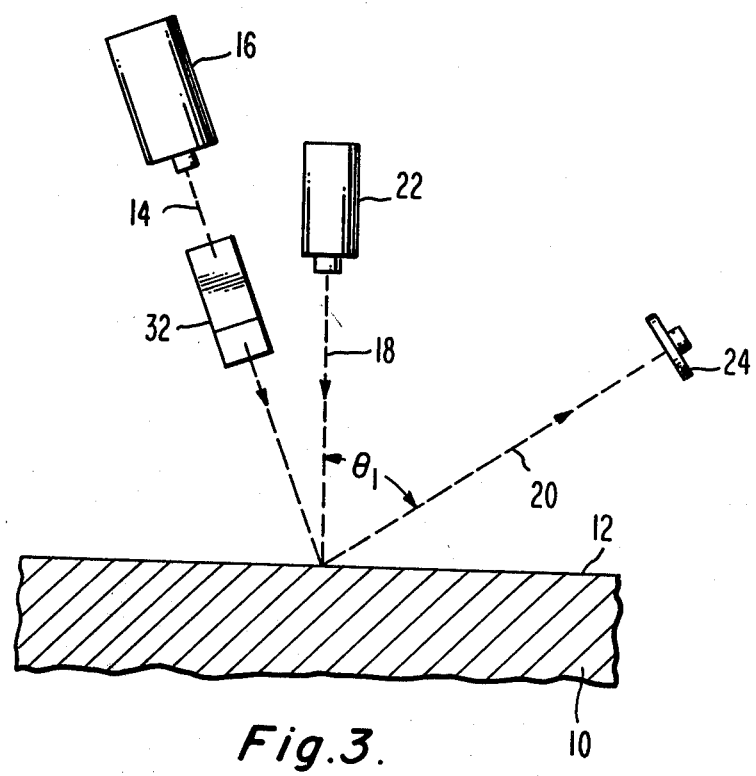
FIG. 3 is a cross-sectional view illustrating diagrammatically a third embodiment of the present novel method.

When the second laser beam 18 strikes the surface 12 uniformly at an angle perpendicular to the plane of the surface 12, as shown in FIG. 3, the surface reflectivity, i.e., the effectiveness of the surface 12 in reflecting the beam 18, may be mathematically expressed as follows:

$$R_\perp \cong \left(\frac{n-1}{n+1}\right)^2 \left(1 - \frac{4n}{n^2-1}\Delta\right)$$

$$\text{where } \Delta = \frac{e^2\lambda_2^2 p}{\pi c^2 n^2 m} = 3.0 \times 10^{-21} p$$

where c is the speed of light, n is the refractive index of the semiconductor lattice, and m is the carrier effective mass. The relative change of $R_\perp$ due to free carriers, which is the signal-to-background ratio, $\Delta_1$ is:

$$\Delta_1 \equiv \frac{\delta R_\perp}{R_\perp} = \frac{4n}{n^2-1}\Delta = 3.9 \times 10^{-21} p$$

Table I provides values for $\Delta$ and $\Delta_1$ at different power levels for the first laser beam 14. The values for $\Delta_1$ as listed in Table I indicate that the effect is measurable, but it requires a rather high-power laser.

Better results may be achieved if the second laser beam 18 is polarized parallel to the plane of incidence, by means of a polarizer 34 as shown in FIG. 1, and strikes the surface 12 uniformly at an angle of incidence $\theta_I$ equal to Brewster's angle defined by the relationship TAN $\theta_1 = n$, where n is the refractive index of the semiconductor substrate 10. If the laser beam 18 is polarized parallel to the plane of incidence, the reflection without induced free carriers can in theory be reduced to zero for the Brewster's angle of incidence, $\theta_B = 73.6$ degrees. The reflectivity at Brewster's angle for a change in refractive index by free carriers, where n=3.4 is:

$$R_B = \frac{1}{4}\left(1 - \frac{1}{n^2}\right)^2 \Delta^2 = 0.21\Delta^2$$

More important than $R_B$ is its ratio to the background, i.e., to the residual reflection (in the absence of free carriers) due to incomplete polarization and to the divergence of the laser beam 18. This signal-to-background ratio is listed in Table I as $\Delta_2 = R_B/R_p + R_\gamma$, where $R_p$ is the background reflection due to incomplete polarization and $R_\gamma$ is the other contribution to the background reflection from the divergence of the laser beam 18. The comparison with $\delta R/R$ for normal incidence, $\Delta_1$, shows the advantage of the Brewster's angle method.

Figure 2:
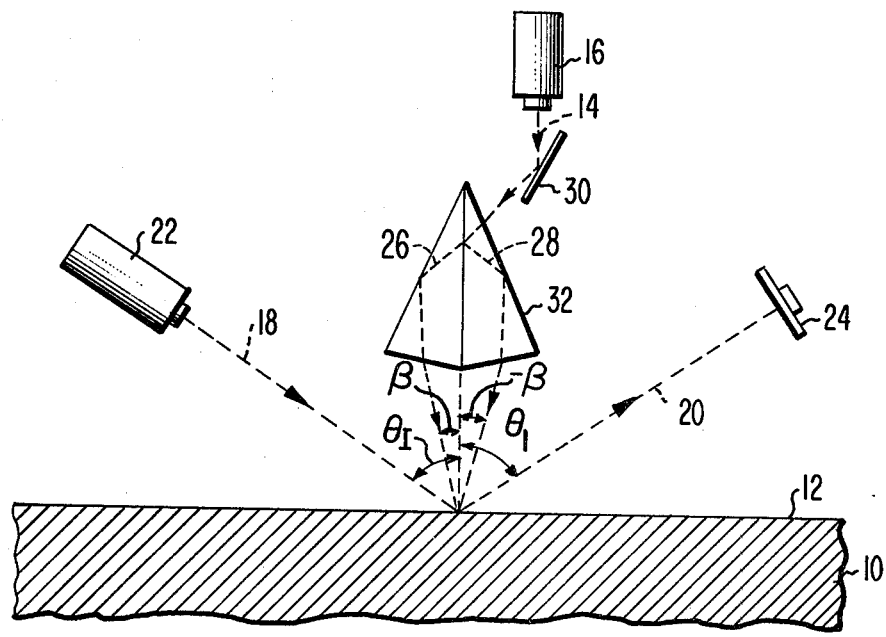
FIG. 2 is a cross-sectional view illustrating diagrammatically another embodiment of the present novel method whereby one of the laser beams is split into two coherent beams.

In order to further discriminate against the high background reflection, one may utilize spatially periodic excitation of the free carriers. The first laser beam 14, prior to irradiating the surface 12, is split into two coherent beams 26 and 28 which are then reunited on the surface 12 at symmetrical angles of incidence $\beta$ and $-\beta$, respectively, as illustrated in FIG. 2. At the area on the surface 12 where the beams 26 and 28 are reunited, electrons and holes are periodically excited by an optical interference pattern with an intensity which varies sinusoidally along the surface 12. The periodicity d is equal to $\lambda_1/2\sin\beta$. The resulting free-carrier concentration then becomes:

$$p = \frac{N_L\tau}{Ah\nu_1 L}\left(1 + \frac{\cos qx}{\sqrt{1+q^2L^2}}\right)$$

where $q = 2\pi/d$

With $\lambda = 0.5$ $\mu$m and $d = L = 30$ $\mu$m, the angle $\beta$ will be about 0.5 degrees, which should be relatively easy to control. In the present embodiment, the first beam 14 is reflected by a mirror 30 into a modified Kösters prism 32, as illustrated in FIG. 2. The modified Kösters prism 32, having coatings designed for approximately equal reflection and transmission, splits the beam 14 into the two coherent beams 26 and 28, which are then reunited at the surface 12. The excited surface 12 presents to the second laser beam 18 a reflection amplitude grating. Assuming that the spots of the two laser beams 14 and 18 on the surface 12 are of equal size and in perfect registration, by utilizing the Fraunhofer diffraction integral to calculate the diffraction pattern, one may obtain the signal-to-background ratio $\Delta_3$ equal to $I(\phi)/I_o$, where $\phi$ is the phase angle. For the first order maxima at $\phi = 2\pi$, one obtains:

$$\Delta_3 \equiv \frac{I(\Delta_1)}{I(o)} = \frac{\Delta_1^2}{16(1+q^2L^2)}\bigg/\left(\frac{2}{N\phi}\right)^2$$

where N is the number of grating lines equal to $\sqrt{A/d}$. For $d \leq L = 30$ $\mu$m and the area of the spot equal to 0.25 mm$^2$, then $$\Delta_3 = 4.23\ \Delta_1^2,$$

which is listed in Table I. The quantity $\Delta_3$ has to be compared with $\Delta_1$ which is the signal-to-background ratio for normal reflection without any diffraction grating. One may conclude from Table I that the grating gives an advantage in signal-to-background ratio for $N_L > 100$ W only.

The relatively poor signal-to-background ratio of the grating technique can be improved considerably if Brewster's angle reflection is used. Inserting the above expression for $R_B$ into the Fraunhofer integral, one obtains:

$$\Delta_4 \equiv \frac{I_B(\Delta)}{I_B(0)} = \frac{\left(1 - \frac{1}{n^2}\right)^2 (\Delta/4)^2}{(R_\gamma + R_p)/(N\pi)^2} \left(\frac{1}{1 + q^2 L^2}\right)$$

For $d \leq L = 30$ μm and the spot area equal to 0.25 mm$^2$, then $$\Delta_4 = 16.9 \Delta_2$$

which is listed in Table I. One may see that a significant improvement is obtained over the no-grating Brewster's angle case for all excitation levels.

The dependence of the signal $I(\Delta_1)$ on the grating periodicity may be used to get a more direct measurement of L, the carrier diffusion length. $I(\Delta_1)$ depends upon the angle $\beta$ of FIG. 2 as follows:

$$I(\Delta_1) \alpha \frac{1}{1 + \left(\frac{16\pi L}{\lambda_1} \sin\beta\right)^2}$$

By varying the angle $\beta$ and thereby the periodicity of the optical interference pattern, the change in the interference of the reflected beam 20 due to this periodicity change may be used to determine the carrier diffusion length in accordance with the above expression.

The present method further comprises the step of measuring the time response of the reflected beam 20 by measuring the intensity decay thereof after the termination of a square pulse of the first laser beam 14. The decay of the free carriers after termination of a square pulse, measured by the time decay of the reflected beam 20 intensity, is a measure of the carrier recombination time, $\tau$, according to the following expression:

$$p = \frac{N_L \tau}{Ah\nu_1 L} erfc\left(\sqrt{t/\tau}\right)$$

This is a slightly faster decay than $\exp(-t/\tau)$. In order to be able to see this decay, the detector 24 must have a resolution better than $\tau$, which is assumed to be about 1 μsec.

The present optical testing method for semiconductors is applicable to testing and monitoring silicon wafers between the various production steps of IC manufacturing, and it should help to increase the factory yield significantly. In summary, I have assumed an excitation wavelength $\lambda_1 = 0.5$ μm from a pulsed dye laser, a probing wavelength $\lambda_2 = 3.39$ μm from an He-Ne laser, and a spot diameter of 0.5 mm. The results depend on the power of the exciting laser, $N_L$, and are listed in Table I in terms of signal-to-background ratios $\Delta_1$, $\Delta_2$, $\Delta_3$, $\Delta_4$ for four variations: (1) uniform excitation and normal reflection, (2) uniform excitation and Brewster's angle reflection, (3) grating-like excitation and normal reflection, and finally (4) grating-like excitation and Brewster's angle reflection. While method (1) requires very high excitation power, it nevertheless appears to be feasible with a pulsed dye laser and a cooled InSb junction detector. Method (2) gives a great improvement over (1) requiring only 10 watts of excitation power. Methods (3) and (4) require less power than Method (1), but involve the added complexity of the grating-like excitation. Changing the grating periodicity by changing the angle between the interfering laser beams allows a more direct determination of the diffusion length. The best signal-to-background ratio can be obtained by method (4) where less than 10 watts should be sufficient for a good signal. Since visible and infrared light is used for excitation and probing, the present technique is applicable for bare semiconductor surfaces as well as surfaces covered with silicon dioxide or other transparent insulating layers. Focusing of the two laser beams 14 and 18 into a small spot allows one to probe and scan small areas of the whole wafer. The present optical technique should provide, rapidly and without touching, significantly improved control over wafer uniformity and perfection between the various wafer fabrication steps.

What is claimed is:

1. A method of optically testing electrical parameters of a surface of a semiconductor including carrier mobility and recombination time comprising the steps of:
   irradiating said surface with a first beam of monochromatic light having a wavelength less than the wavelength corresponding to the band-gap energy of said semiconductor, whereby the energy of said light beam is substantially absorbed by said surface resulting in the excitation of electrons and holes at said surface,
   simultaneously irradiating said surface with a second beam of monochromatic light having a wavelength larger than the wavelength corresponding to the band-gap energy of said semiconductor, whereby part of said second beam is reflected from said surface,
   measuring the intensity of said reflected beam, whereby the magnitude thereof is a measure of the carrier mobility and recombination time at said semiconductor surface.

2. A method as recited in claim 1 wherein the step of irradiating said surface with said first beam is performed by pulsing said first beam in a manner such that the average power stays below about 10 milliwatts.

3. A method as recited in claim 2 further comprising the step of measuring the time response of said reflected beam by measuring the intensity decay thereof after the termination of a square pulse of said first beam, whereby the time decay of said intensity measurement is a measure of the carrier recombination time.

4. A method as recited in claim 3 wherein said second beam of monochromatic light irradiates said surface uniformly at an angle perpendicular to the plane of said surface.

5. A method as recited in claim 4 further comprising the step wherein said first beam, prior to irradiating said surface, is split into two coherent beams which are then reunited on said surface at symmetrical angles of incidence $\beta$ and $-\beta$, respectively, whereby said electrons and holes at said surface are periodically excited by an optical interference pattern which varies sinusoidally along said surface.

6. A method as recited in claim 5 wherein the periodicity of said optical interference pattern is varied by varying the angle $\beta$, whereby the change in the intensity of said reflected beam is a measure of the carrier diffusion length in said semiconductor.

7. A method as recited in claim 3 wherein said second beam of monochromatic light is polarized parallel to the plane of incidence and strikes said surface uniformly at an angle of incidence $\theta_1$ equal to Brewster's angle, defined by the relationship TAN $\theta_1 =$ n, where n is the refractive index of said semiconductor.

8. A method as recited in claim 7 further comprising the step wherein said first beam, prior to irradiating said first surface, is split into two coherent beams which are then reunited on said surface at symmetrical angles of incidence $\beta$ and $-\beta$, respectively, whereby said electrons and holes at said surface are periodically excited by an optical interference pattern which varies sinusoidally along said surface.

9. A method as recited in claim 2 wherein said semiconductor is silicon, said first beam is a pulsed dye laser beam having a wavelength of about 0.5 micrometers, and said second beam is an infrared He-Ne laser beam having a wavelength of about 3.39 micrometers.

10. A method as recited in claim 2 wherein said measuring step is performed by utilizing an InSb junction detector placed at an angular position to receive said reflected beam.

* * * * *